(12) United States Patent
Hegazi et al.

(10) Patent No.: US 8,455,845 B2
(45) Date of Patent: Jun. 4, 2013

(54) METHOD FOR DETECTING DRAG REDUCER ADDITIVES IN GASOLINE

(75) Inventors: Ezzat M. Hegazi, Windsor (CA); Maha A. Al-Sayegh, Saudi Aramco (SA)

(73) Assignee: Saudi Arabian Oil Company, Dhahran (SA)

( * ) Notice: Subject to any disclaimer, the term of this patent is extended or adjusted under 35 U.S.C. 154(b) by 218 days.

(21) Appl. No.: 12/861,608

(22) Filed: Aug. 23, 2010

(65) Prior Publication Data
US 2012/0043477 A1 Feb. 23, 2012

(51) Int. Cl.
G01J 1/58 (2006.01)
G01T 1/167 (2006.01)
G01N 21/64 (2006.01)

(52) U.S. Cl.
USPC ............ 250/459.1; 250/301; 250/461.1

(58) Field of Classification Search
USPC ............ 250/459.1, 573, 301, 458.1, 461.1
See application file for complete search history.

(56) References Cited

U.S. PATENT DOCUMENTS

| | | | |
|---|---|---|---|
| 5,049,738 A * | 9/1991 | Gergely et al. ............ 250/301 |
| 5,656,810 A * | 8/1997 | Alfano et al. ............ 250/301 |
| 5,739,916 A * | 4/1998 | Englehaupt ............ 356/414 |
| 5,990,484 A * | 11/1999 | Ohsuka ............ 250/458.1 |
| 6,810,718 B2 * | 11/2004 | Wilson et al. ............ 73/54.01 |
| 2002/0030812 A1 * | 3/2002 | Ortyn et al. ............ 356/326 |
| 2002/0121611 A1 * | 9/2002 | Yokokawa et al. ........ 250/458.1 |
| 2003/0141459 A1 | 7/2003 | Hegazi et al. |
| 2004/0246479 A1 * | 12/2004 | Cartlidge et al. ............ 356/335 |
| 2007/0237679 A1 | 10/2007 | Hegazi |
| 2008/0035858 A1 | 2/2008 | Hegazi |

OTHER PUBLICATIONS

Hegazi, Ezzat, Detection of Drag Reducing Agents (DRAs) in Fuels Using Laser Induced Fingerprints, Saudi Aramco Journal of Technology, Winter 2010, pp. 34-37.
Hegazi, Ezzat, Laser Invention is Used to Fingerprint Oil, www.jobsataramco.eu/66/, Feb. 3, 2010, Dhahran.
PCT International Search Report Dated Oct. 17, 2011; International Application No. PCT/US2011/045713; International Filing Date Jul. 28, 2011; Applicant: Saudi Arabian Oil Company.

* cited by examiner

Primary Examiner — David Porta
Assistant Examiner — Faye Boosalis
(74) Attorney, Agent, or Firm — Bracewell & Giuliani LLP

(57) ABSTRACT

A method for detecting polymer-based drag reducer additives in gasoline includes placing a sample in a high UV-transmittance receptacle having at least two transparent adjacent sides and irradiating the same with a pulsed laser beam; detecting laser-induced fluorescence wavelength resolved spectrum at a 90° angle relative to the laser beam through the adjacent side of the receptacle and a slit in a diffraction screen adjusting the position of the receptacle and de-focusing the collimating lenses so that the low resolution fluorescence wavelength-resolved spectrum appears with a first peak at about 380 nm and a second peak at about 430 nm; recording the laser-induced fluorescence wavelength-resolved spectra within a defined time-gate starting at the end of the temporal span of the laser pulse; and comparing the percentage intensity of the first peak relative to the second peak to that of a gasoline sample free of any polymer-based drag reducer additives.

10 Claims, 6 Drawing Sheets

METHOD FOR DETECTING DRAG REDUCER ADDITIVES IN GASOLINE

BACKGROUND OF THE INVENTION

1. Field of the Invention

This invention relates to detecting polymer-based drag reducer additives in a gasoline sample.

2. Description of the Related Art

Polymer-based drag reducer additives are made of long chained poly-alpha-olefin polymers with ultra-high molecular weight (larger than 1-million Daltons). When injected into a stream of gasoline fuels traveling through pipelines, drag reducer additives enhances the flow of the stream by reducing effect of drag of the liquid from the pipeline walls. This, in turn, creates better streamlining for the flow in the pipe and ultimately leads to significant reductions in the cost of pipeline shipping.

As drag reducer additives injected gasoline fuels travel through pipelines, the long-chained drag reducer additives become subjected to gradual breakage mainly due to the mechanical shearing action within the pumps and pipelines. Usually, the amount of drag reducer additives to be injected in the pipeline is estimated in a way that ensures total dissipation of the long-chained polymers from the transported fuel by the time the fuel reaches its ultimate destination. In practice, however, the long-chained polymers do not totally disappear by the time they reach their end destination. There will always be some amount of intact long-chain drag reducer additives polymers remaining in the gasoline fuel at the final destination in addition to other amounts of sheared and/or partially sheared polymers.

In multi-fuel pipelines, i.e. pipelines utilized in transporting different types of gasoline fuels in sequence, extra care must be taken to achieve zero levels of drag reducer additives before transporting aviation jet fuel in particular, because aviation rules forbid the use of drag reducer additives in turbine fuel. To clean the pipeline down to zero-levels of drag reducer additives after it had been used for other drag reducer additives injected fuels the pipeline is usually flushed with some amount of drag reducer additives free fuel, such as gasoline.

A method for detecting the presence and/or concentration of drag reducer additives in gasoline fuel is based on size exclusion techniques such as gel-permeation chromatography which is relatively complicated, lengthy and expensive. The detection limit of this chromatography technique is about 1-2 PPM and can be further enhanced down to 0.2 PPM if the sample is evaporated to increase the concentration percentage of drag reducer additives. Other techniques to detect and remove drag reducer additives from gasoline fuels use absorption materials such as carbon and clay. Detection of drag reducer additives is complicated when the drag reducer additives are used with gasoline fuels. Due to the use of dilute polymeric hydrocarbons as drag reducer additives, they are indistinguishable from gasoline fuel using many of standard detection methods. In addition, drag reducer additives has no UV chromophores and, as such, it does not fluoresce when irradiated by UV light leading to challenges in using photo-optical methods for detection.

What is needed is a cost-effective method for detecting the presence and the concentration of drag reducer additives in a gasoline sample with accuracy in the PPM range. To be cost effective, it would be advantageous to provide an apparatus and method that does not require time-consuming evaporation to reach PPM accuracy, by measuring the relative intensities of specific time-gated laser-induced fluorescence fluorescence spectra that fall outside the temporal convolution area. This method can be fast and capable of detecting drag reducer additives levels in gasoline sample down to sub PPM without resorting to any evaporation procedure.

SUMMARY OF THE INVENTION

One embodiment of the invention is a method for detecting the concentration of polymer-based drag reducer additives in gasoline, the method including the following: (a) placing a gasoline sample in a receptacle having at least two adjacent clear sides and irradiating one of the two clear sides of the receptacle with a pulsed laser beam, the pulsed laser beam having a wavelength in the ultra violet region shorter than 300 nm; (b) detecting laser-induced fluorescence wavelength resolved spectrum at 90° angle relative to the incident laser beam and through a slit defined in a diffraction screen, the diffraction screen being placed at a pre-defined first distance from the receptacle; (c) adjusting the position of the receptacle and slightly de-focusing the collimating lenses so that the low resolution fluorescence wavelength-resolved spectrum of the gasoline sample appears with a first peak at about 380 nm and a second peak at about 430 nm; (d) recording the laser-induced fluorescence wavelength-resolved spectra of the gasoline sample within a defined time-gate starting at the end of the temporal span of the laser pulse; and (e) comparing the percentage intensity of the first peak relative to the second peak for the laser-induced fluorescence spectrum near 380 nm of the gasoline sample to that of a gasoline sample free of any polymer-based drag reducer additives. In another embodiment of the method, the location of the diffraction-screen is at the pre-defined distance of between 0.5 mm to 2 mm from the side of the receptacle. In another embodiment of the method, the time-gate in step (d) is of 3 ns width and starting immediately after the end of the laser pulse. In another embodiment of the method, the following steps are added: (a) repeating steps (a) through (e) with a control sample that is free of drag reducer additives; and (b) comparing the percentage intensities of the gasoline sample with the control sample.

Another embodiment of the present invention is a method of estimating the concentration of polymer-based drag reducer additives in an unknown sample of gasoline, the method including the following: (a) detecting the laser-induced fluorescence spectra within a first time-gate and a second time-gate for the gasoline sample to produce a first recorded intensity of spectra measured at the first time-gate and a second recorded intensity of spectra measured at the second time-gate; (b) normalizing the first recorded intensity of spectra to unity at the highest peak while those of the second time-gate are plotted relative to them without being normalization; (c) determining the areas-under-the-curves of the first and second recorded spectra in a particular wavelength range; (d) calculating the area-under-the-curve ratio of the first recorded spectrum relative to the second recorded spectrum using the normalized numbers; (e) repeating steps (a) through (d) above for a first control sample and a second control sample, each control sample being prepared with a pre-known drag reducer additives concentrations in gasoline, and (f) applying curve fitting relative to the first and second recorded spectra to produce a calibration curve for those pre-known samples, and then using the calibration curve to estimate the drag reducer additives concentration of the unknown gasoline sample. In another embodiment of the method, the first of the two narrow time-gates starts immediately after the end of the laser pulse and the second narrow time-gate starts 6 ns after the end of the laser pulse for a calibration curve in the 0-1 PPM range. In another embodiment of the method, the first of the two narrow time-gates starts immediately after the end of the laser pulse and the second narrow time-gate starts 9 ns after the end of the laser pulse for a calibration curve in the 1-10 PPM range. In another embodiment of the method, the intensities of the laser-induced fluorescence spectra are normalized to unity at the second peak near 430 nm. In another embodiment of the method, the intensities of the laser-induced fluorescence spectra are normalized to unity at the second peak near 430 nm. In another embodiment of the method, the areas-under-the-curves in steps (c) and (d) are in a spectral range near the first peak near 380 nm.

BRIEF DESCRIPTION OF THE DRAWING

So that the manner in which the above-recited features, aspects and advantages of the invention, as well as others that will become apparent, are attained and can be understood in detail, more particular description of the invention briefly summarized above can be had by reference to the embodiments thereof that are illustrated in the drawings that form a part of this specification. It is to be noted, however, that the appended drawings illustrate some embodiments of the invention and are, therefore, not to be considered limiting of the invention's scope, for the invention can admit to other equally effective embodiments.

DETAILED DESCRIPTION

As used herein, the term "gasoline sample" means any gasoline.

The term "drag reducer additives" means any polymer-based drag reducer additive. In another embodiment, the characteristic of drag reducer additives is that it is non fluorescing when exposed to UV light. In another embodiment, the characteristic of drag reducer additives is that it does not produce anti-Stokes, Stokes, or resonance luminescence.

The term "receptacle" means a container that holds the gasoline sample for testing. In one embodiment, the receptacle has the characteristics of having high transmittance to ultraviolet (UV) radiation. In another embodiment, the receptacle can be in the shape of a conventional cuvette. In another embodiment, the receptacle is a rectangular-type quartz cuvette with clear windows on all four sides and having a path-length of approximately 1 cm, a width of approximately 1 cm, and a height of approximately 5 cm.

The term "PPM" means parts per million.

Figure 1:
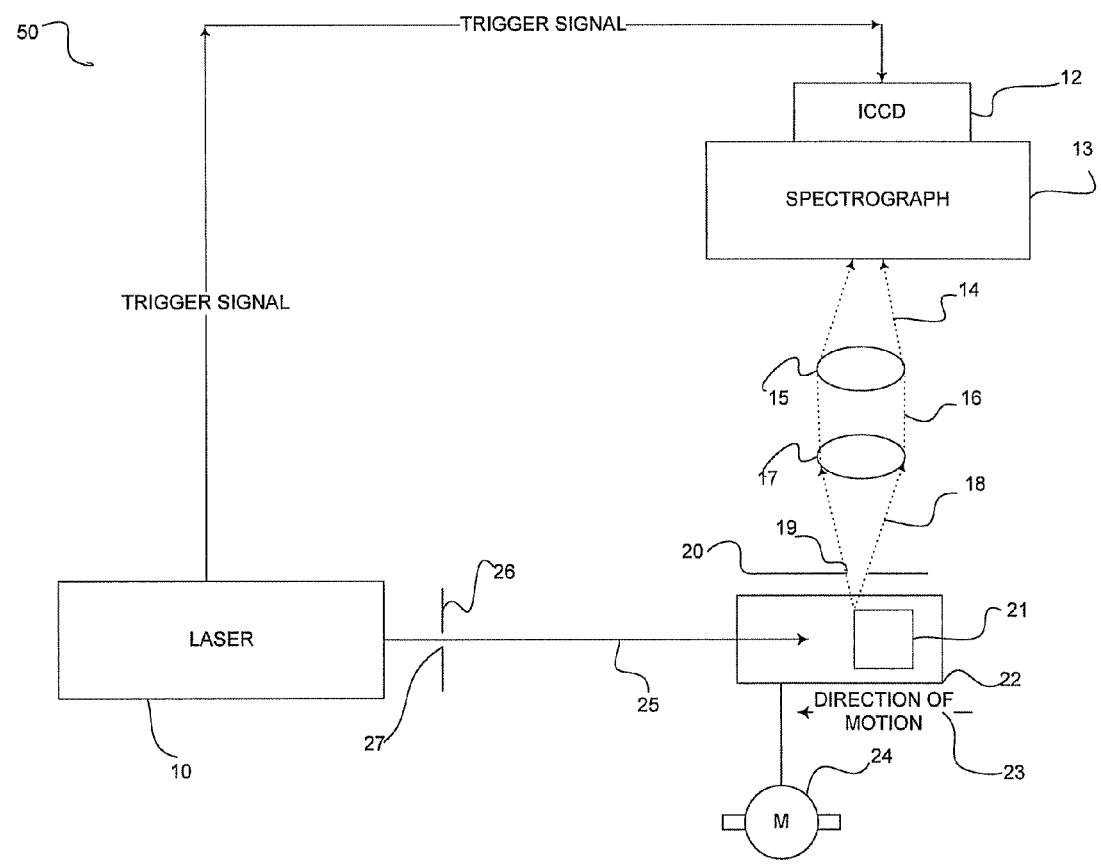
FIG. 1 is a block diagram of the apparatus for measuring concentrations of fuel mixtures using depth-resolved laser-induced fluorescence according to the present invention.

With reference to FIG. 1, the apparatus 50 for detecting drag reducer additives in gasoline using depth-resolved laser-induced fluorescence performs measurements on a receptacle 21 holing a gasoline sample. The receptacle 21 is formed from an optically transparent and chemically inert material, such as quartz, fused silica, or other material having a high transmittance to ultraviolet radiation ("UV") and may be in the form of a conventional cuvette, test tube or the like. In one embodiment, the receptacle 21 is a quartz cuvette having a length of approximately one centimeter, a width of approximately one centimeter, and a height of approximately five centimeters.

The receptacle 21, containing a sample, is mounted on a moveable stage 22, which moves linearly along a first axis. The moveable stage 22 may be L-shaped, including a vertical support and horizontal support. The moveable stage 22 may be formed from Plexigals plates or any other suitable material, and holds the receptacle 21 through use of a fastener, such as a clamp, a flexible, elastic band, or other suitable releasable fastener.

The moveable stage 22 may be made to move in the path 23 of the excitation light beam in any desired manner. In one embodiment, the horizontal support of moveable stage 22 is mounted on a track and is actuated to move along the track by step motor 24. Step motor 24 moves the moveable stage in defined increments of about 0.16 mm. Alternatively, moveable stage 22 may be provided with mechanical means for moving the receptacle 21 in the path 23 of the excitation light beam. For example, the horizontal support of moveable stage may have a rack mounted thereon operated by a pinion or gear train operable by a vernier dial, a thumbwheel, a slider or the like, which may be equipped with a precision scale or with detents corresponding to 0.16 mm increments of movement in the path of the beam.

As shown in FIG. 1, moveable stage 22 moves towards laser 10, so that the distance between the receptacle 21 and the laser 10 increases or decreases during measurement, according to the depth measurements desired. It should be understood that apparatus 50 may have any suitable light source capable of fluorescing gasoline sample. However, in one embodiment, a pulsed dye laser is utilized to generate a single-frequency coherent beam, thus reducing the occurrence of backscattering of unwanted frequencies of light. Alternatively, an ultraviolet lamp, such as a Xenon lamp with a monochromator to adjust the excitation wavelength, may be used in place of laser 10.

As shown in FIG. 1, laser 10 generates a laser beam 25, which travels along the first axis to penetrate transparent receptacle 21 and generate fluorescence within the gasoline sample. Laser beam 25 may be shaped and directed by a conventional optical iris 27, formed through a screen 26, as shown. Iris 27 is selected for a desired beam diameter, depending upon the needs of the user. The moveable stage 22 moves with respect to the support surface, which may be, for example, an optical bench, an enclosed fluorometer housing, or the like. The moveable stage 22 with the receptacle 21 moves independently of the diffraction slit 20. The diffraction slit 20 is always fixed in one place.

Diffraction screen 20 has a vertical slit 19 formed therethrough for diffracting the fluoresced light emitted by the gasoline sample. The generated laser-induced fluorescence in the gasoline sample diffracts in all directions, however, because of the diffraction screen 20 allows only the portion of the fluorescence that propagates at an angle close to 90° relative to the direction of the impinging laser beam that passes through the vertical slit 19. The diffracted light beam (illustrated by dashed arrows 18) passes along a second axis, substantially orthogonal to the first axis, and impinges upon a collimating lens 17 to form a relatively and substantially unidirectional light beam 16. Light beam 16 passes through a focusing lens 15 to form a slightly de-focused beam 14, which is received by spectrograph 13. Lenses 17 and 15 may be any suitable lenses. However, in one embodiment, lenses 17 and 15 are convex quartz lenses. In one embodiment, the collimating lens 17 is a bi-convex quartz lens and the focusing 15 is a plano-convex quartz lens, both of suitable focal lengths and thicknesses to ensure slight de-focusing of the fluorescence light onto the opening of a spectrograph. The fluorescent emission is depth-resolved in that only the florescence from a particular depth within receptacle 21 passes through the stationary vertical slit 19 to the frequency separator of the spectrograph 13, so that, in theory, only the fluorescence emitted by a thin vertical layer of the gasoline sample in the receptacle 21 passes through vertical slit 19.

An exemplary spectrograph 13 is the Sciencetech® 8010 spectrograph. The dispersed light from the spectrograph 13 is passed to an intensified Charge Couple Device (ICCD) 12. ICCD 12 preferably has a fast time response and resolution of about 1.5 ns. One exemplary ICCD is the Stanford Computer Optics 4 Quick E® ICCD.

It should be noted that laser 10 is a pulsed laser. As such, ICCD 11 is triggered by the Q-switch of the laser 10. As shown in FIG. 1, the laser 10 may be in electrical communication with the ICCD 11. Laser 10 generates a trigger signal so that ICCD 11 has an appropriate excitation signal to compare to the corresponding emission signal from photomultiplier tuber 12. In one embodiment, the laser is a Nd:YAG laser with frequency-doubling crystals that generates 266 nm radiation. For such a laser, the energy output is held at a fixed value of 30-50 mJ per pulse, though other energy ranges may be utilized. The width of the pulse is approximately 6-8 ns and the energy is 30-50 mJ per pulse. The laser 10 generates a pulsed ultraviolet (UV) laser beam 25, penetrates the receptacle and generates fluorescence within the gasoline sample. An optical filter can be placed in front of the Nd:YAG laser head to cut off the infrared and green radiations originating from the fundamental and second harmonic wavelengths of the frequency-doubling crystals. An adjustable iris can be placed in the path of the laser beam, before impinging on the gasoline sample in the receptacle, to adjust the size of the laser beam impinging onto the side of the receptacle depending upon the need of the user.

When a fluorescing gasoline sample, in receptacle 21, is irradiated with UV radiation, it emits light at a wavelength longer than that of the excitation wavelength. The characteristics of the emitted fluorescence spectrum, i.e., its shape, spectral region, temporal behavior, etc., depend not only on the type and the concentrations of the individual chemical compounds, but also on the geometry of the sample illumination. The bulk of the liquid sample, which may be modeled as a succession of thin layers, each stacked upon the other, receives non-uniform excitation radiations at each layer and, consequently, each layer emits a distinct fluorescence spectrum. The non-uniform excitation radiations associated with each layer occur mainly because of the reduction in the intensity of the excitation laser radiation with path length as the laser light beam penetrates inside the gasoline sample, and also because of the reabsorption of the already emitted fluorescence from the adjacent layers caused by the fluorescent emission of one compound occurring at the excitation wavelength of a second compound.

The apparatus 50 may be utilized as follows. The sample holder 21 is fixed at a desired depth setting and the spectrograph/ICCD 13/12 combination is used to obtain the emission spectrum. For the exemplary devices, dimensions and wavelengths given above, the spectrograph has a slit size of approximately 0.5 mm and produces dispersion in a spectral region that includes 380 nm and 440 nm.

Figure 2:
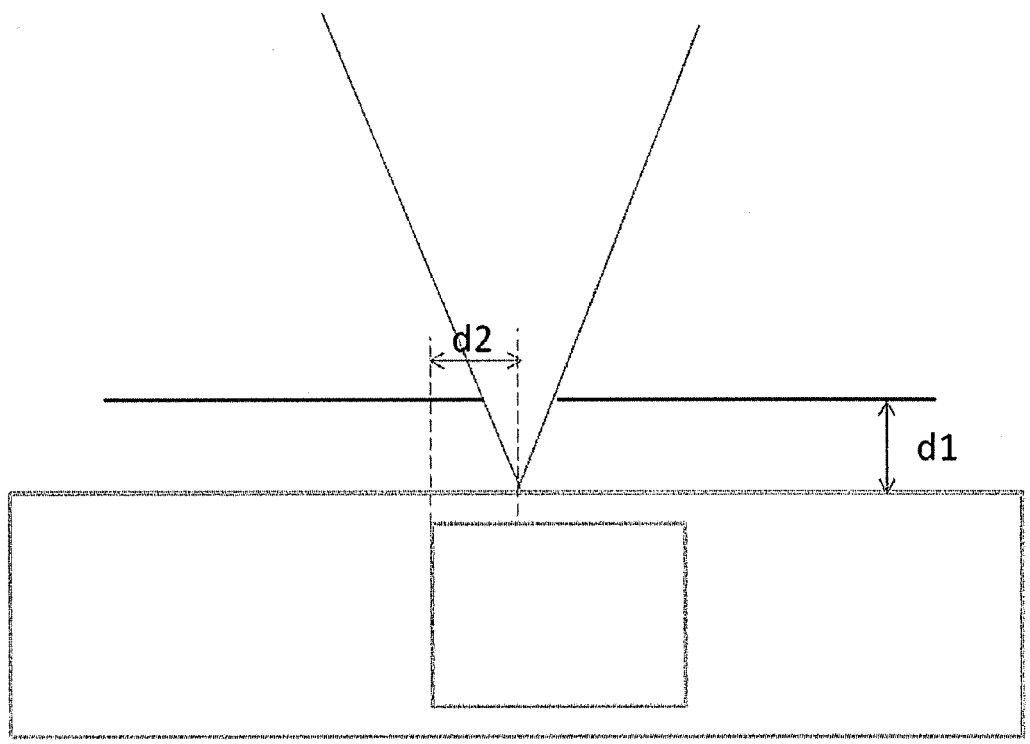
FIG. 2 provides a graphic illustration of the positions of the receptacle and diffraction slit which are enlarged for clarification. The pre-defined distance referred to here is identified as d1 while the position to be adjusted is d2.

FIG. 2 provides a graphic illustration of the positions of the receptacle and diffraction slit are enlarged for clarification. The pre-defined distance referred to here is identified as d1 in FIG. 2. The position to be adjusted is d2 in FIG. 2.

In one embodiment, a method of detecting drag reducer additives in gasoline which is being, or has been, transported through pipelines from refineries to storage tanks or any other destination. The gasoline in this case is in its final compositional form which includes all necessary enhancement additives and color dye. In another embodiment, a typical laser-induced fluorescence spectroscopy setup is employed. The gasoline sample is irradiated with pulsed UV laser beam and the laser-induced fluorescence from the sample is detected at 90°-angle to the incident laser beam. The wavelength of the incident laser radiation should be shorter than 300 nm. A dispersing device such as a diffraction grating spectrograph coupled with a time-gated detection device such as a photomultiplier or intensified charge coupled device is then used to measure the intensity of the wavelength-resolved laser induced fluorescence in a short spectral range between approximately 380 nm and 440 nm, which includes two prominent peaks on the resulting laser-induced fluorescence spectra from the gasoline sample. The locations of the peaks depend on the resolution of the detection system used, such as the diffraction grating in the spectrograph, the number of pixels in the ICCD, and also on the slight deviation from the exact optical alignment. The measurement of the laser-induced fluorescence intensity can be carried out within narrow time-gates of approximately 3-ns width. One narrow time-gate located immediately after the end of the laser pulse is sufficient to give qualitative information as to whether drag reducer additives contamination in sub PPM is present or not. This is done by comparing the intensity of the laser-induced fluorescence gasoline sample spectrum near 380 nm to that of a drag reducer additives free sample. In addition, quantitative estimates of the drag reducer additives concentrations between 0 PPM and 10 PPM can be deduced if the laser-induced fluorescence spectrum is measured also at a second narrow time-gate, typically 6 ns or 9 ns after the end of the laser pulse. This is done by measuring the ratio of the areas-under-the-curves, preferably between 380 nm and 410 nm, of the laser-induced fluorescence spectra that have been measured at the two different time-gates.

In one embodiment, the gasoline sample, to be tested for whether it contains drag reducer additives, is placed in a receptacle. Each of the subsequent measurements is conducted using the same receptacle. The receptacle is mounted on a fixed platform behind a diffraction screen having a vertical slit whose width and location, once adjusted, are kept fixed relative to the location of the receptacle at all times. In a preferred embodiment, the slit width of the diffraction screen is approximately 1.5 mm and is located at a distance of approximately 0.5 mm from the inner edge of the receptacle wall at which the laser is impinging.

The spectrograph is a part of the fluorescence detection system and is used to disperse the fluorescence light in terms of its wavelength-resolved spectral components. The intensities of these dispersed spectral components are then measured by a suitable photo-detector sensor, which is the second part of the detection system. Examples of a suitable photo-detector sensor are (a) a combination of a single photomultiplier coupled with a scannable mechanism for the diffraction grating of the spectrograph to allow the photomultiplier to measure the intensities of the individual wavelength-resolved components in sequence, (b) a sensitive photodiode array or (c) an intensified charge coupled device employing one- or two-dimensional channel plate. All three options can be time-gated with time resolution of 1-5 ns and can have a way to digitally analyze the signal, whether by using an external signal analyzer instrument or a built-in capability within the detection system. In one embodiment, the detection system is a spectrograph coupled to an intensified charge coupled device ("ICCD") having a fast rise time of less than 1.5 ns, time-gated electronics of 1.5-ns resolution, and intrinsic signal analysis capability. The wavelength resolution of the ICCD is approximately 3-4 nm. The ICCD is triggered by the Q-switch of the pulsed YAG laser whose pulse rate is kept fixed at 10 Hz.

In one embodiment, the method of detecting the presence of drag reducer additives and its concentration in the gasoline sample relies on making intensity comparisons between certain areas on the laser-induced fluorescence spectra of the gasoline sample when measured at specific narrow time-gates. The laser-induced fluorescence spectrum of gasoline is found to change in shape as the diffraction-screen slit changes its location. The location of the slit can first be located at a position that produces a gasoline spectrum with two prominent peaks near 380 nm and 430 nm. The positions of the peaks and their intensity stabilities depends on many factors including the diffraction slit width, its location, and the collection optics alignment with respect to the spectrograph/ICCD detection unit.

In one embodiment, if the gasoline sample is contaminated with any amount of drag reducer additives (>0.1 PPM) the intensity of the laser-induced fluorescence spectrum near 380 nm will drop relative to that near 430 nm. In another embodiment, quantitative information about the drag reducer additives concentration can be deduced by relating the intensities of certain areas on the spectrum at two narrow time-gates. One of the time-gates is located immediately at the end of the temporal span of the laser pulse and the other at a few ns later.

In another embodiment, the width of the time-gates is 3 ns and the location of the first time-gate is immediately after the end of the laser pulse while the location of the second time-gate is either 6 or 9 ns later depending on the concentration range of drag reducer additives in the gasoline sample. For sub PPM levels of drag reducer additives in the gasoline sample (i.e., in the range between 0.1-1 PPM), the optimum location of the second narrow time gate is 6 ns after the first time-gate while for the PPM levels (i.e., in the range between 1-10 PPM), the optimum location is 9 ns after the first time-gate. For convenience, the laser-induced fluorescence spectra measured immediately after the end of the laser pulse with time-gate width 3 ns will be designated as 0S3, while those measured 6 ns and 9 ns after the end of the laser pulse with time-gate width of 3 ns each will be designated as 6S3 and 9S3, respectively.

When measuring the laser-induced fluorescence spectra of commercial drag reducer additives free gasoline having octane grade 91 with dark green coloring additive dye and other standard additives using the present setup, two distinct peaks are visible—one at a approximately 383 nm and the other at approximately 430 nm. If a gasoline sample is contaminated with drag reducer additives of any amount >0.1 PPM, then the peak at 383 nm drops in intensity relative to the peak at 430 nm when compared to a non contaminated gasoline sample.

In another embodiment, the concentration of drag reducer additives contamination in a gasoline sample in the two ranges (1 PPM-10 PPM) and (0.1 PPM-1 PPM) can be determined. The laser-induced fluorescence spectra measured at two different time-gates are used together with specific calibration plots which are constructed using pre-known drag reducer additives concentrations for the receptacle. Two sets of drag reducer additives concentrations are to be prepared by using serial dilutions of solid drag reducer additives in gasoline. Solid drag reducer additives are then dissolved in gasoline of grade 91-octane by means of a magnetic stirrer that is kept running overnight. The drag reducer additives concentrations in PPM of the two sets is then determined at various concentrations for each set. Both sets are then left for more than 24 hrs before measurements are taken.

Two groups of wavelength-resolved fluorescence spectra are measured for five representative samples of set 1 containing various concentrations of drag reducer additives. One group is measured immediately after the end of the laser pulse with a time-gate width of 3 ns, and the second group is measured 9 ns after the end of the laser pulse with the same 3-ns time-gate width. The spectra are presented in such a way so that all the higher intensity curves are unified in intensity at the 430 nm wavelength, while each of the curves in the lower intensity plotted relative to its corresponding higher intensity curve. The reason for plotting them this way is to bring to light the effect the drag reducer additives has on the 9-ns gasoline spectra, which can decrease in intensity as the concentration of drag reducer additives is increased.

In another embodiment, two groups of wavelength-resolved fluorescence spectra can be measured for four representatives of gasoline with 0, 0.1, 0.3, and 1 PPM concentration of drag reducer additives. In a similar manner as noted above, the higher-intensity group can be measured immediately after the end of the laser pulse, while the lower-intensity group can be measured 6 ns after the end of the laser pulse. The time-gate width in both groups can be kept fixed at 3 ns. The reason for choosing 6-ns instead of 9-ns is merely to optimize the observed effect when dealing with lower drag reducer additives concentrations.

EXAMPLES

Figure 3:
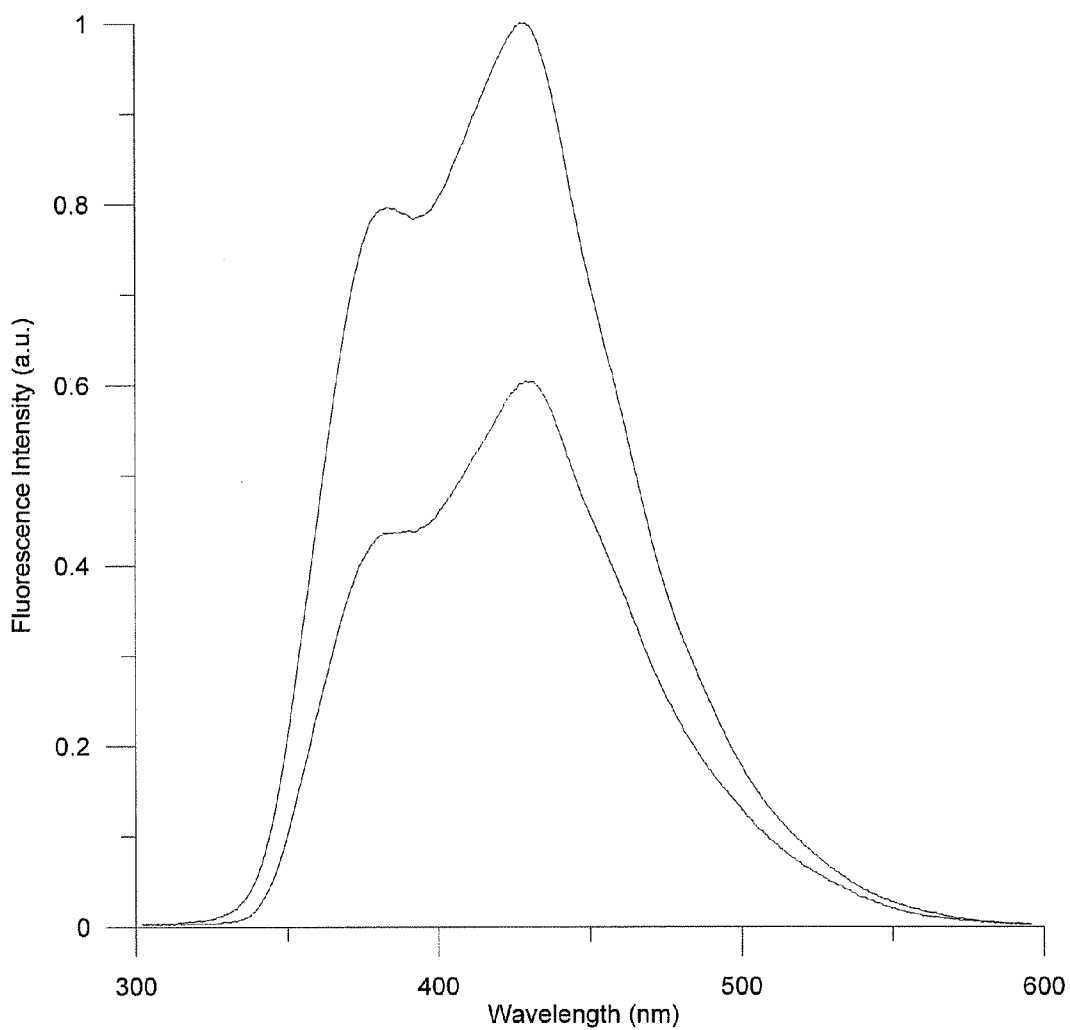
FIG. 3 is a drawing of the low resolution laser-induced fluorescence spectra for a gasoline sample free of drag reducer additives measured at two narrow time-gates of 3-ns width each, one starting immediately after the end of the laser pulse and the other starting 6 ns after the end of the laser pulse. The intensities of the two curves are plotted relative to each other.

Examples of the laser-induced fluorescence spectra are shown in FIG. 3, which are for commercial drag reducer additives-free gasoline having octane grade 91 with dark green coloring additive dye and other standard additives. Both spectra in FIG. 3 were measured within time-gates of 3 ns each. The top spectrum is 0S3 and the bottom spectrum is 6S3. The two distinct peaks on each spectrum are at approximately 383 nm and 430 nm. The first part of the method maintains that, on the 0S3 spectrum, a gasoline sample is contaminated with drag reducer additives of any amount >0.1 PPM if the peak at 383 nm drops in intensity relative to the peak at 430 nm when compared to a non contaminated gasoline sample.

Preparation of Known Drag Reducer Additives Concentrations in Gasoline Samples

In the following examples the gasoline samples were supplied by the Dhahran refinery of Saudi Aramco Oil Company and had included the standard dark green dye and all other standard additives such as antioxidant, metal deactivator, deposit control additive, and MTBE. Two sets of drag reducer additives concentrations were prepared by using serial dilutions of solid drag reducer additives in gasoline. The solid drag reducer additives were prepared from ConocoPhilips "brand RP2" by freeze drying the liquid commercial product, which originally comprised of drag reducer additives suspended in a liquid solvent matrix. An amount of 5 mg of the solid drag reducer additives were dissolved in 500 ml commercial motor gasoline of grade 91-octane by means of a magnetic stirrer that was kept running overnight. The drag reducer additives concentrations in PPM of the two sets were as follows:

Set 1: (0, 0.5, 1, 2, 3, 4, 5, and 10)
Set 2: (0, 0.05, 0.1, 0.2, 0.3, and 0.4)

Both sets were left for more than 24 hrs before measurements were made.

Figure 4:
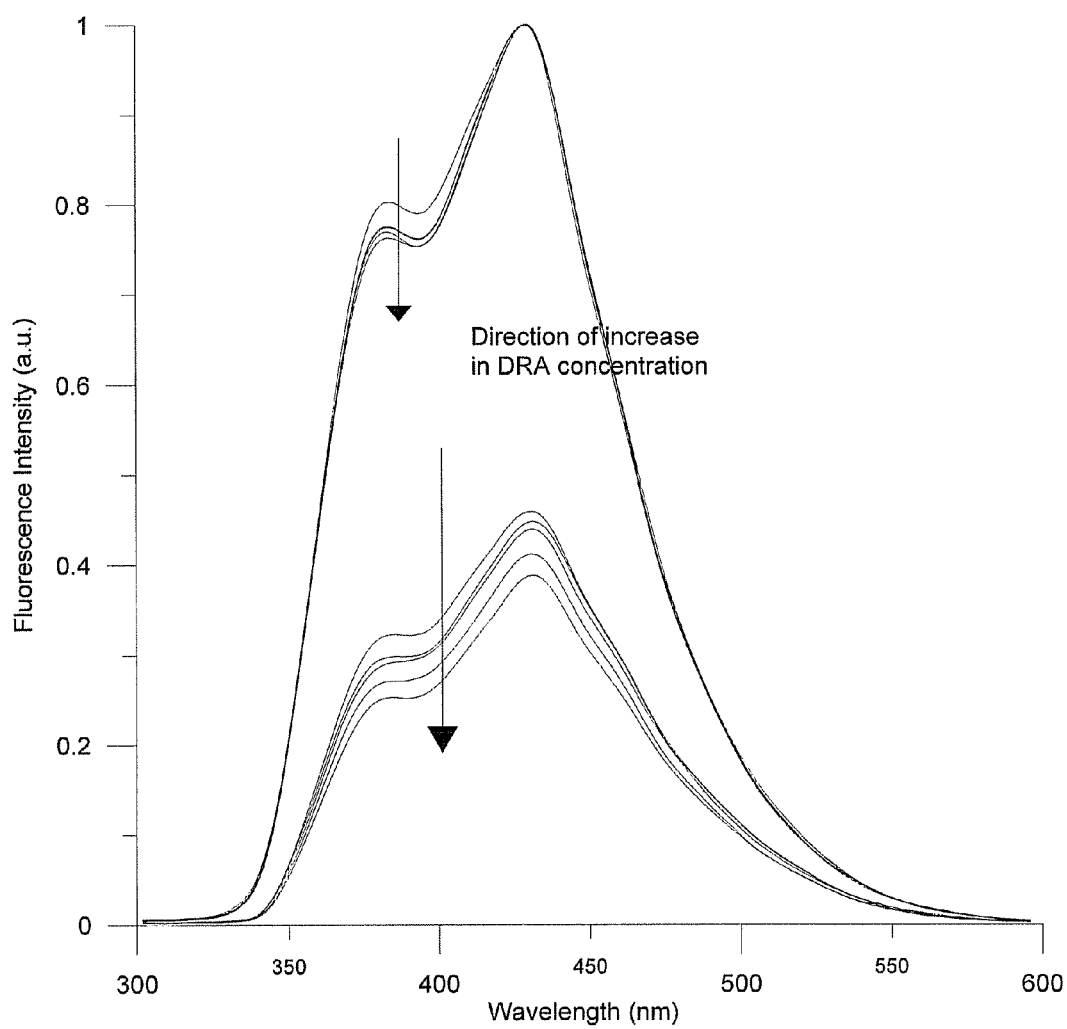
FIG. 4 is a graphic illustration of the low resolution laser-induced fluorescence spectra for gasoline samples with drag reducer additives concentrations of 0, 0.5, 1, 5, and 10 PPM, measured at two narrow time-gates; one immediately after the end of the laser pulse and the other 9 ns after the end of the laser pulse. The intensities of the first time-gate spectra are normalized to unity at the highest peak while those of the second time-gate are plotted relative to them without being normalized.

Fluorescence Measurements of PPM Level of Drag Reducer Additives in Gasoline Samples Referring to FIG. 4, there is shown two groups of wavelength-resolved fluorescence spectra for five representative samples of set 1; gasoline with 0, 0.5, 2, 5, and 10 PPM drag reducer additives. One group; i.e., 0S3, is measured immediately after the end of the laser pulse with a time-gate width of 3 ns, and the second group; i.e., 9S3, is measured 9 ns after the end of the laser pulse with the same 3-ns time-gate width. The spectra are presented in such a way that all the higher intensity curves; i.e., the 0S3 spectra, are unified in intensity at the 430 nm wavelength, while each of the curves in the lower intensity group; i.e., the 9S3 spectra, is plotted relative in intensity to its corresponding curve in the 0S3 group. The reason for plotting them this way is to bring to light the effect the drag reducer additives has on the 9-ns gasoline spectra, which can be seen to decrease in intensity as the concentration of drag reducer additives is increased. The order of the 9-ns spectra of FIG. 4 from top to bottom is 0, 0.5, 2, 5, and 10 PPM.

Figure 5:
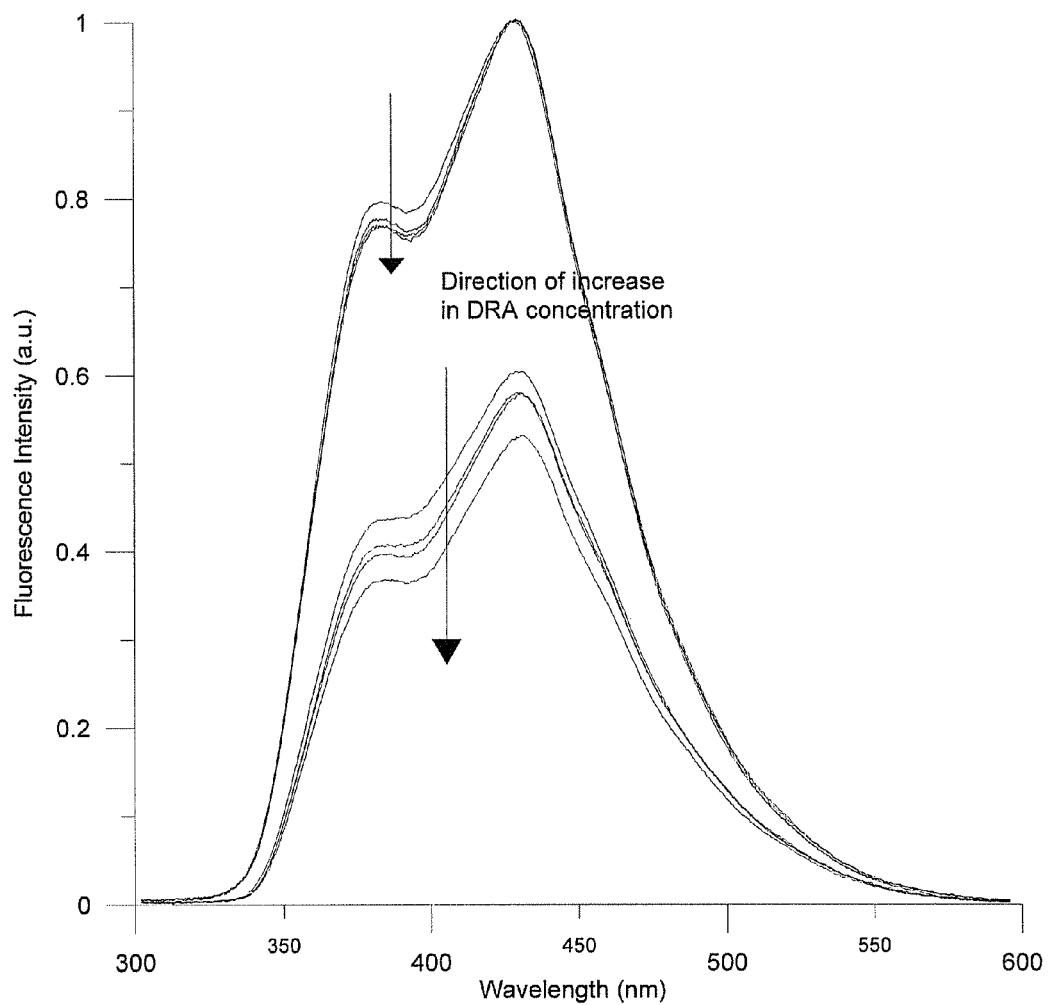
FIG. 5 is a graphic illustration of the low resolution laser-induced fluorescence spectra for gasoline samples with drag reducer additives concentrations of 0, 0.1, 0.3, and 1 PPM, measured at two narrow time-gates; one immediately after the end of the laser pulse and the other 6 ns after the end of the laser pulse. The intensities of the first time-gate spectra are normalized to unity at the highest peak while those of the second time-gate are plotted relative to them without being normalized. The normalized numbers are used so that all numbers can be relative to one another. For example: in the DRA-free sample (the blank sample) the areas belonging to the first and second time gates are 5 and 4, while those for the DRA-contaminated sample are 10 and 7. Once the areas belonging to the first gate in both samples (5 and 10) are normalized to 1 then the area belonging to the second gate for the blank sample (4) will be 0.8 and that for the DRA-contaminated sample (7) will be 0.7.

Fluorescence Measurements of Sub PPM Level of Drag Reducer Additives in Gasoline Samples Referring to FIG. 5, there is shown two groups of wavelength-resolved fluorescence spectra for four representatives of set 2; namely, gasoline with 0, 0.1, 0.3, and 1 PPM concentration of drag reducer additives. In a similar manner as above, the higher-intensity group was measured immediately after the end of the laser pulse; i.e., 0S3, while the lower-intensity group was measured 6 ns after the end of the laser pulse; i.e., 6S0. The time-gate width in both groups was kept fixed at 3 ns as before. The reason for choosing 6-ns instead of 9-ns is merely to optimize the observed effect when dealing with lower drag reducer additives concentrations. As in FIG. 4, the 0S3 spectra in FIG. 5 are plotted with their intensities unified at the 430 nm wavelength while the 6S3 are plotted relative in intensity to their counterparts of the earlier time-gate, from which it can be seen also that the overall intensities of the 6-ns time-gate gasoline spectra decrease with drag reducer additives concentration in gasoline. The order of the 6-ns spectra of FIG. 5 from top to bottom is 0, 0.1, 0.3, and 1 PPM.

It is possible to construct linear calibration curves relating the drag reducer additives concentrations in gasoline to the intensities of the time-gated laser-induced fluorescence spectra. However, these linear fits can only be done for small ranges of concentrations, which is the reason behind splitting up the drag reducer additives concentration into two sets. For convenience, the areas-under-the-curves between 383 nm and 410 nm for the 0S3, 6S3, and 9S3 spectra will be designated as 0A3, 6A3, and 9A3, respectively.

FIG. 5 is a graphic illustration of the laser-induced fluorescence spectra for gasoline samples with drag reducer additives concentrations of 0, 0.1, 0.3, and 1 PPM, measured at two narrow time-gates; one immediately after the end of the laser pulse and the other 6 ns after the end of the laser pulse. The intensities of the first time-gate spectra are normalized to unity at the highest peak while those of the second time-gate are plotted relative to them without being normalized.

Figure 6:
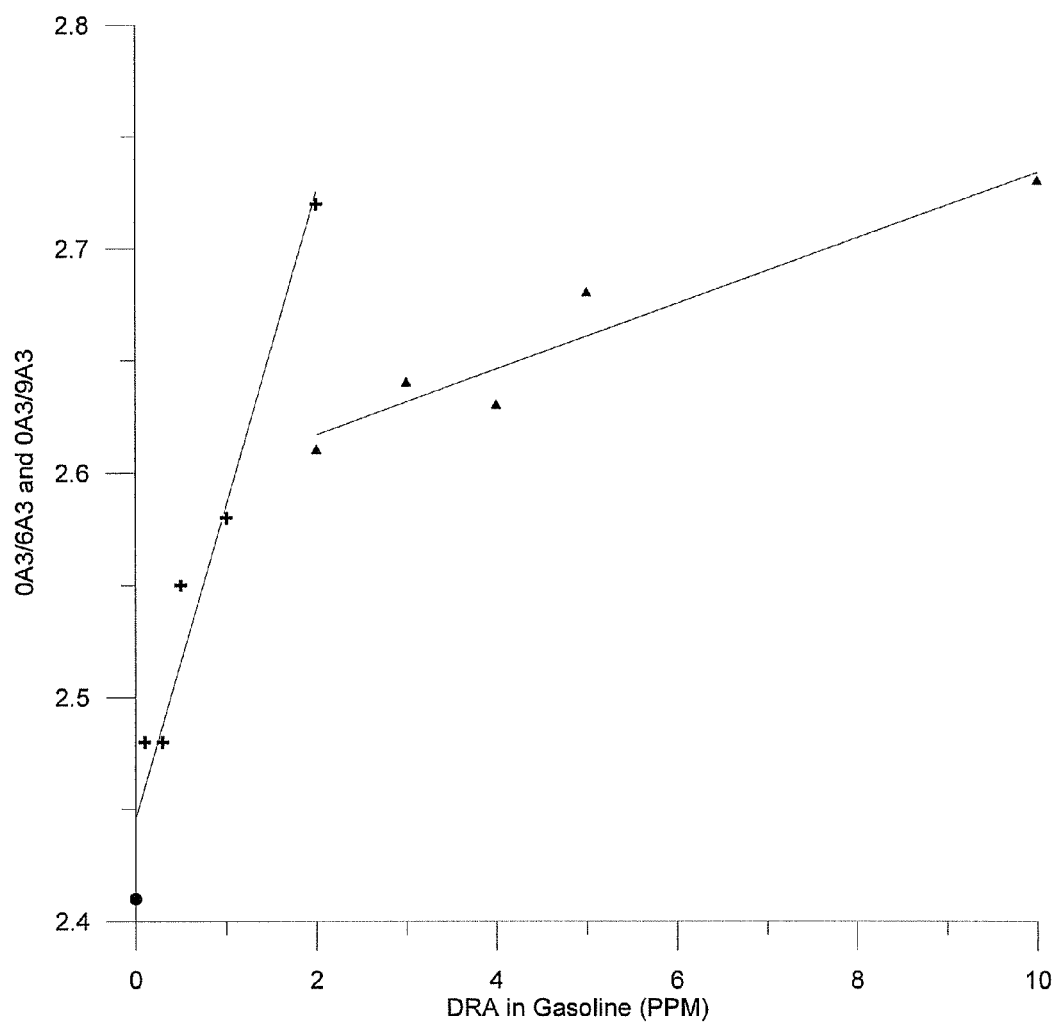
FIG. 6 depicts two plots relating ratios of areas-under-the-curve, in the 383 nm-410 nm spectral range, to drag reducer additives concentration in gasoline samples. One plot represents best linear fit for drag reducer additives concentrations from 2 PPM to 10 PPM (triangles), and the other represents best linear fit for drag reducer additives concentrations from 0.1 PPM to 2 PPM (pluses). The time-gates for both sets of data are different, the former is 6 ns after the end of the laser pulse while the latter is 9 ns after the end of the laser pulse.

With reference to FIG. 6, it is shown such two linear calibration curves that have been constructed by plotting the 0A3/9A3 and 0A3/6A3 ratios as functions of drag reducer additives concentration in gasoline for sets 1 and 2, respectively, and then have been subjected to standard linear regression fitting. The resulting coefficients of determination for the linear regression; i.e. $r^2$, are 0.92 for the first set of drag reducer additives concentrations and 0.95 for the sub-PPM set of concentrations. It should be noted that in the first concentration set the fitting started from 2 PPM and not from 0 PPM.

While the invention has been shown in only a few of its forms, it should be apparent to those skilled in the art that it is not so limited but susceptible to various changes without departing from the scope of the invention. Accordingly, it is intended to embrace all such alternatives, modifications, and variations as fall within the spirit and broad scope of the appended claims.

Those skilled in the art will recognize that many changes and modifications can be made to the method of practicing the invention without departing the scope and spirit of the invention. In the drawings and specification, there have been disclosed embodiments of the invention and, although specific terms are employed, they are used in a generic and descriptive sense only and not for the purpose of limitation, the scope of the invention being set forth in the following claims. The invention has been described in considerable detail with specific reference to these illustrated embodiments. It will be apparent, however, that various modifications and changes can be made within the spirit and scope of the invention as described in the foregoing specification. Furthermore, language referring to order, such as first and second, should be understood in an exemplary sense and not in a limiting sense. For example, it can be recognized by those skilled in the art that certain steps can be combined into a single step.

We claim:

1. A method for detecting the concentration of polymer-based drag reducer additives in gasoline, the method comprising the steps of:
   a. placing a gasoline sample in a high UV-transmittance receptacle having at least two transparent adjacent sides and irradiating the sample through one of the two transparent sides of the receptacle with a pulsed UV laser beam;
   b. detecting laser-induced fluorescence wavelength resolved spectrum at a 90° angle relative to the incident laser beam from the sample through the adjacent side of the receptacle and a slit defined in a diffraction screen, the diffraction screen being placed at a pre-defined distance from the adjacent side of the receptacle;
   c. adjusting the position of the receptacle and slightly defocusing the collimating lenses so that the low resolution fluorescence wavelength-resolved spectrum of the gasoline sample appears with a first peak at about 380 nm and a second peak at about 430 nm;
   d. recording the laser-induced fluorescence wavelength-resolved spectra of the gasoline sample within a defined time-gate starting at the end of the temporal span of the laser pulse; and
   e. comparing the percentage intensity of the first peak relative to the second peak for the laser-induced fluorescence spectrum of the gasoline sample to that of a gasoline sample free of any polymer-based drag reducer additives.

2. The method of claim 1, wherein the UV laser beam wavelength is shorter than 300 nm.

3. The method of claim 1, wherein the location of the diffraction-screen is at the pre-defined distance of between 0.5 mm to 2 mm from the adjacent side of the receptacle.

4. The method of claim 1, wherein the time-gate in step (d) is of 3 ns width and starting immediately after the end of the laser pulse.

5. The method of claim 1, the method further comprising the steps of:
   a. repeating steps (a) through (e) with a control sample that is free of drag reducer additives; and
   b. comparing the percentage intensities of the gasoline sample with the control sample.

6. A method of estimating the concentration of polymer-based drag reducer additives in an unknown sample of gasoline, the method comprising the steps of:
   a. detecting the pulsed UV laser-induced fluorescence spectra within a first time-gate and a second time-gate for the gasoline sample to produce a first recorded intensity of spectra measured at the first time-gate and a second recorded intensity of spectra measured at the second time-gate;
   b. normalizing the first recorded intensity of spectra to unity at the highest peak while those of the second time-gate are plotted relative to them without being normalization;
   c. determining the areas-under-the-curves of the first and second recorded spectra in a particular wavelength range;
   d. calculating the area-under-the-curve ratio of the first recorded spectrum relative to the second recorded spectrum using the normalized numbers;
   e. repeating steps (a) through (d) above for a first control sample and a second control sample, each control sample being prepared with a pre-known drag reducer additives concentrations in gasoline,
   f. applying curve fitting relative to the first and second recorded spectra to produce a calibration curve for those pre-known samples, and then using the calibration curve to estimate the drag reducer additives concentration of the unknown gasoline sample.

7. The method of claim 6, wherein the first of the two narrow time-gates starts immediately after the end of the laser pulse and the second narrow time-gate starts 6 ns after the end of the laser pulse for a calibration curve in the 0-1 PPM range.

8. The method of claim 6, wherein the first of the two narrow time-gates starts immediately after the end of the laser pulse and the second narrow time-gate starts 9 ns after the end of the laser pulse for a calibration curve in the 1-10 PPM range.

9. The method of claim 6, wherein the intensities of the laser-induced fluorescence spectra are normalized to unity at the second peak near 430 nm.

10. The method of claim 6, wherein the areas-under-the-curves in steps (c) and (d) are in a spectral range near the first peak near 380 nm.

* * * * *